United States Patent [19]
Buboltz et al.

[11] Patent Number: 5,171,241
[45] Date of Patent: Dec. 15, 1992

[54] DEVICE FOR FOLDING AN INTRAOCULAR LENS AND HOLDING IT IN THE FOLDED STATE

[75] Inventors: David C. Buboltz, Rancho Cucamonga; Charles F. Hornback, Riverside, both of Calif.

[73] Assignee: Ioptex Research Inc., Calif.

[21] Appl. No.: 503,302

[22] Filed: Apr. 2, 1990

Related U.S. Application Data

[63] Continuation-in-part of Ser. No. 404,127, Sep. 7, 1989, abandoned, which is a continuation-in-part of Ser. No. 364,269, Jun. 9, 1989, abandoned.

[51] Int. Cl.$^5$ .............................................. A61B 17/00
[52] U.S. Cl. ........................................ 606/1; 606/107; 623/6
[58] Field of Search ......................... 606/107, 1; 623/6; 206/0.8, 5.1, 5

[56] References Cited

U.S. PATENT DOCUMENTS

| | | |
|---|---|---|
| 4,173,281 | 11/1979 | Trought . |
| 4,257,521 | 3/1981 | Poler . |
| 4,615,703 | 10/1986 | Callahan et al. . |
| 4,681,102 | 7/1987 | Bartell ..................................... 606/1 |
| 4,697,697 | 10/1987 | Graham et al. . |
| 4,736,836 | 4/1988 | Alongi et al. . |
| 4,781,719 | 11/1988 | Kelman . |
| 4,819,631 | 4/1989 | Poley . |

Primary Examiner—C. Fred Rosenbaum
Assistant Examiner—William W. Lewis
Attorney, Agent, or Firm—Rosenman & Colin

[57] ABSTRACT

A device is described for folding an IOL and thereafter holding it in its folding state, which comprises a member foldable into two sections of substantially equally dimensions, each of said sections having a shoulder portion dimensioned to receive an edge of the optic of an unfolded IOL and to hold the IOL in the plane of the member when the member is in an unfolded state. A method of folding a foldable IOL along the diameter thereof comprises placing said IOL in the device of claim 1 so that the edges of the optic rest on the shoulders and the optic is substantially centered along the fold line of said member, and folding said sections together.

A case is also described for the device which is capable of holding the device with an IOL in an unfolded state.

30 Claims, 11 Drawing Sheets

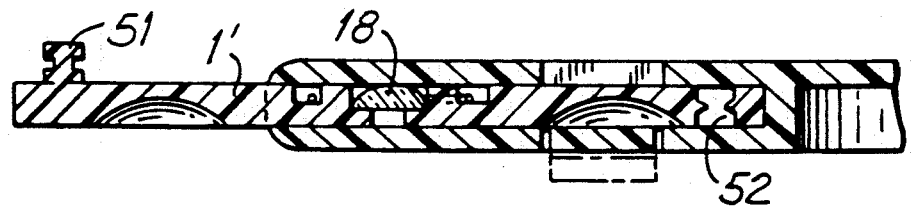
FIG. 16
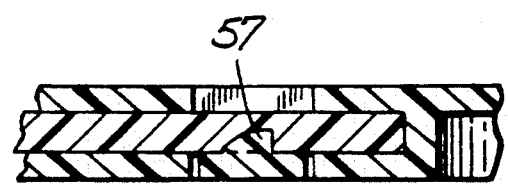
FIG. 17
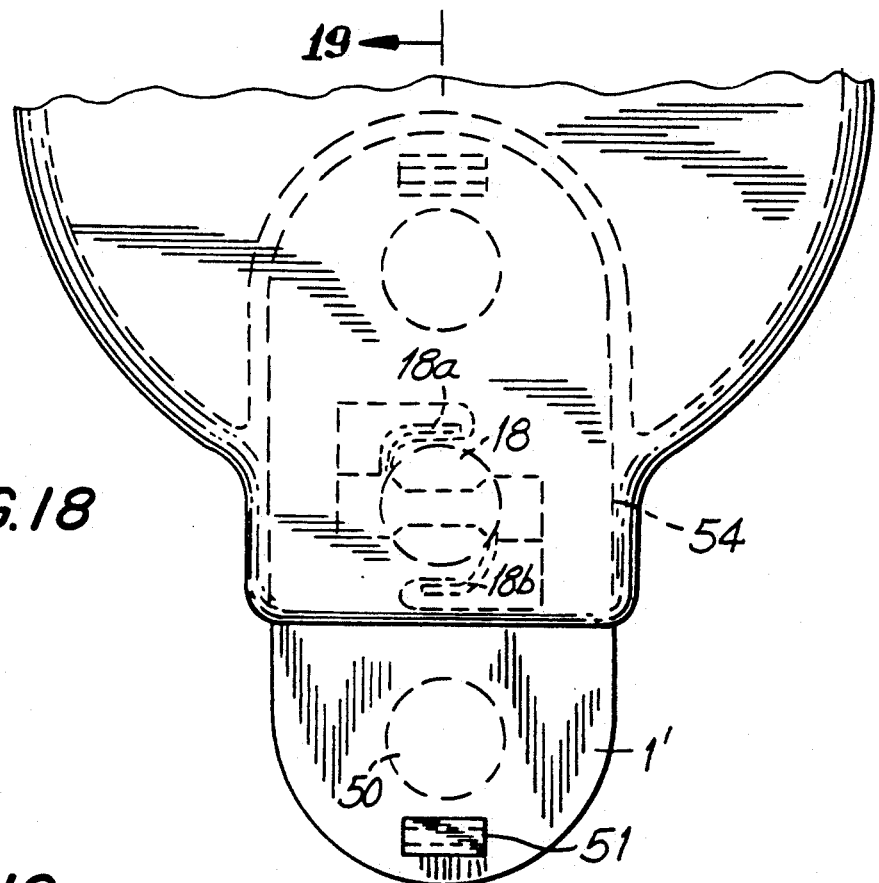
FIG. 18
FIG. 19
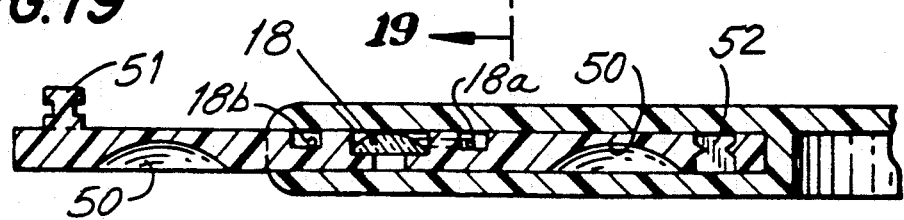

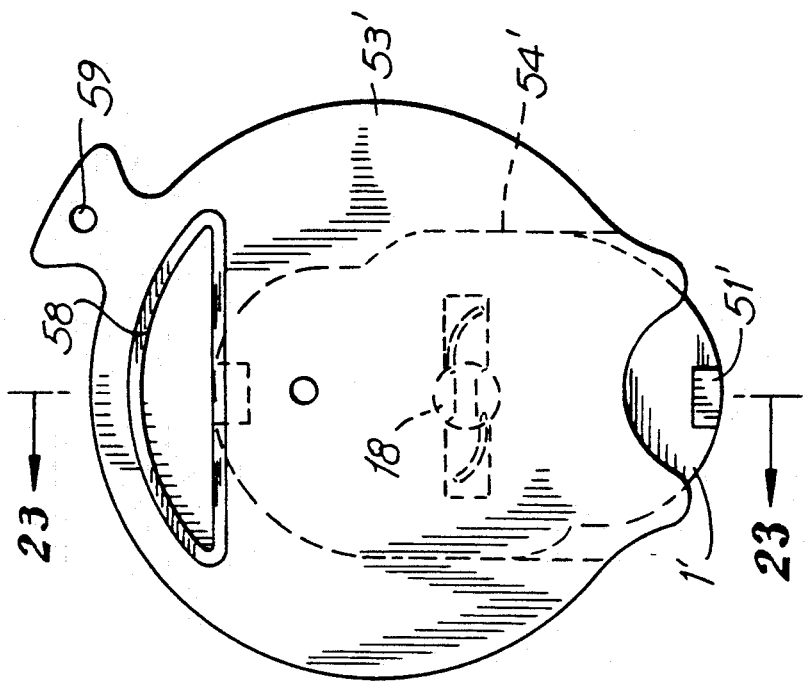
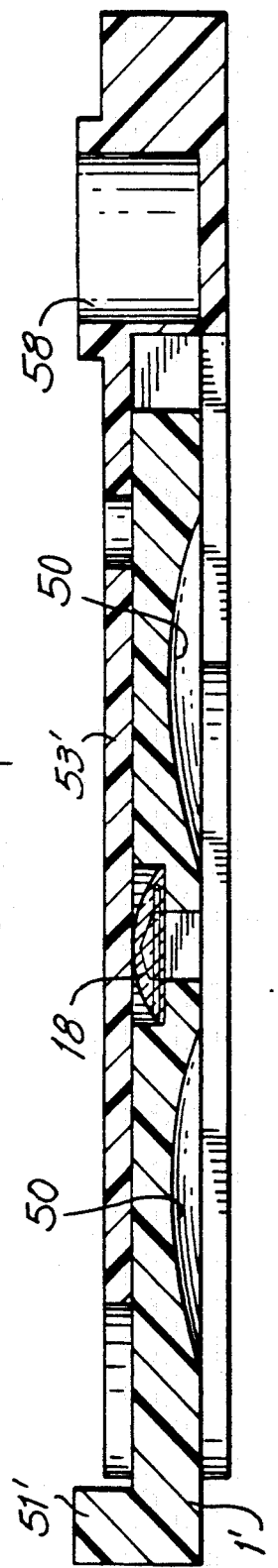

DEVICE FOR FOLDING AN INTRAOCULAR LENS AND HOLDING IT IN THE FOLDED STATE

This is a continuation-in-part of our copending application Ser. No. 404,127 filed Sep. 7, 1989 which is a continuation-in-part of our copending application Ser. No. 364,269, filed Jun. 9, 1989 both now abandoned. The present invention relates to a device for folding an intraocular lens (IOL) and thereafter holding it in its folded state and to a method of folding a foldable IOL utilizing a device according to the present invention.

In order to reduce to a minimum, the size of the incision through which IOLs are inserted during surgical implantation, the use of deformable elastic IOLS has been proposed. An improved form of such an IOL and a tool for folding and inserting such an IOL are described in U.S. Pat. No. 4,834,750 and U.S. patent application Ser. No. 255,131 respectively, assigned to the same assignee as this patent application and which are hereby incorporated by reference.

Other apparatus and devices for folding IOLs are described in U.S. Pat. Nos. 4,473,650; 4,573,998; 4,681,102; 4,715,373; 4,747,404; 4,759,359; 4,769,034; and 4,819,631. Several of such devices include forceps for folding in half and holding deformable elastic IOLs for insertion into an eye during IOL implant surgery. In order to fold such an IOL, commercially available forceps include large parallel tongs for gripping and folding the IOL. To have the strength necessary to fold an IOL body, the tongs of such forceps are relatively bulky. Other forceps having smaller and more delicate gripping tongs do not have sufficient strength to fold most deformable elastic IOLs. Further, in practice it is very difficult to accurately fold an IOL along its diameter to reduce to a minimum the size of the folded IOL. Accordingly, there is a need for an apparatus and method to simply and more accurately fold IOLs along their diameters and for holding such folded IOLs so that they can be gripped by small and delicate forceps which may be efficiently inserted through incisions of the smallest possible size during IOL implant surgery. The devices and methods of the present invention satisfy such needs.

More particularly, the present invention comprises a device for folding an IOL and thereafter holding it in its folded state, which comprises a member foldable into two sections of substantially equal dimensions, each of said sections having a shoulder portion dimensioned to receive an edge of the optic of an unfolded IOL and to hold the IOL in the plane of the member when the member is in an unfolded state.

According to a further embodiment of the present invention the device further comprises a slot substantially symmetrically disposed along a portion of the fold line of the member.

According to a further embodiment of the present invention the slot extends beyond the shoulder portions. The shoulder portions maybe any suitable geometrical configuration, for example, semicircular, triangular or rectangular.

According to a further embodiment of the present invention, the slot of the device of the present invention begins at the outer edge of the member and extends beyond the shoulders. The sections of the member may be beveled along the fold line of the member to facilitate folding the member into two substantially equal sections.

According to a further embodiment of the present invention the slot is disposed about the area of the shoulders so that the shoulders are centrally disposed within the slot.

According to a further embodiment of the present invention the beveled portion of each section is on the side which lies on the outside of said device when the device is in a folded state. The device according to the present invention may also include means for locking the device in the folded position.

The present invention also includes the device as above described in combination with a case which is suitable for transporting or shipping the device having an IOL which is either in a substantially flat configuration, i.e., unfolded therein or has a folded IOL therein.

The case comprises a base for supporting the member and a top secured to the base in a foldable manner, and means for securing the device in the case whereby in use the top folds over, covers and secures the folded IOL.

According to a further embodiment of the present invention the case further comprises IOL stabilizing means extending from the base through the slot adjacent the IOL.

According to a further embodiment of the present invention the device has an opening through each section and the case further comprises means having a configuration on one portion to match the periphery of the optic, the means extending from one of the base or top made with openings in the device to secure the device in the case.

According to a further embodiment of the present invention the combination of the device and the case further comprises a second IOL stabilizing means attached to the top of the case for securing the IOL in the device when the top is folded over the base.

The device of the present invention may also be placed in a case suitable for transporting the device having an unfolded IOL therein which case has a slot therein for receiving the device with the IOL therein, the slot being configured to enable a portion of the device to be griped for removal while retaining the device within the slot until it is desired to remove it. The device may be held within the case either by a friction fit between the device and the slot in the case, or by means of a release member which is capable of locking the device within the slot and releasing it when desired.

The present invention also includes a method of folding a foldable IOL along a diameter thereof which comprises placing an IOL in any of the embodiments of the above described device so that the edges of the optic rest on the shoulders and the optic is substantially centered along the fold line of the member, and folding the sections together.

BRIEF DESCRIPTION OF DRAWINGS

FIG. 16 is a section taken along lines 16/16 of FIG. 14.

FIG. 17 is a section taken along lines 17/17 of FIG. 14.

FIG. 18 is an enlarged partial view of the device in a case where the device is held by a friction fit.

FIG. 19 is a section taken along lines 19/19 of FIG. 18.

FIG. 22 shows a device according to the present invention fitted within the case of FIG. 21.

FIG. 23 is a section along lines 23/23 of FIG. 22.

As shown in FIGS. 1 and 2, the device of the present invention comprises a member 1 foldable into two sections 10 and 12 of substantially equal dimensions such as along a hinge line 16 joining the sections of the member. The foldable member 1 is a made of any suitable foldable material such as molded or milled plastic. If desired it may have hinge means 14 which can, for example, be a hinge line formed along a bevelled portion of each section of said member 1. The section portions are substantially coplanar when the device is in an unfolded condition to receive IOL 18 as illustrated in FIG. 1. The hinge means 14 is constructed to allow the sections to fold together into a folded condition as illustrated in FIG. 2. Preferably the hinge means 14 is a V-shaped channel in a bottom surface of the member leaving a narrow strip of plastic material along the hinge line 16 joining the sections.

Figure 1:
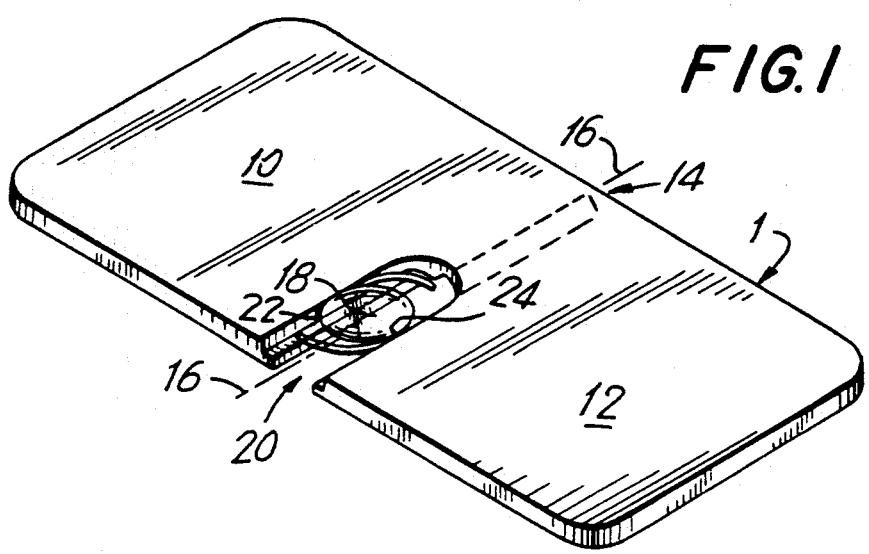
FIG. 1 is a perspective view of a first embodiment of the device of the present invention in an unfolded condition holding an IOL.
Figure 2:
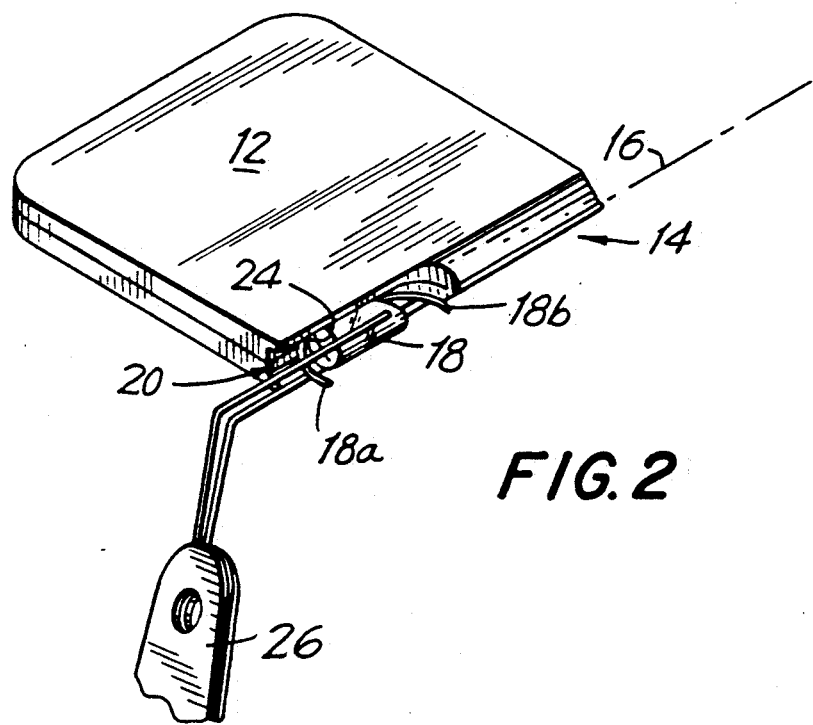
FIG. 2 is a perspective view of the device of FIG. 1 in a folded condition with forceps gripping the folded IOL for removal from the device.

In the embodiment of the invention shown in FIGS. 1 and 2, the device includes a slot 20 in and between the sections 10 and 12 along and symmetrical relative to the hinge line 16. According to this embodiment the slot is open at one side of the sections 10 and 12 and has relieved upper edge portions defining opposing semicircular shoulders 22 and 24. The shoulders are shaped to receive and support opposing edge portions of the IOL optic or lens body 18 and to hold the optice in the plane of sections when the device is in its unfolded condition. The shoulders may be of any convenient geometrical configuration. While they are shown here as semicircular, they can also be triangular or rectangular. The slot 20 also extends along the hinge line 16 on either side of the shoulders to receive haptics 18a and 18b extending from the IOL optic 18 when it is supported by the shoulders. The shoulders support the IOL optic 18 such that the major axis or a diameter thereof lies along or is directly over the hinge line 16. Thus supported, when the device is folded as shown in FIG. 2, the IOL optic folds simply and accurately above the hinge line and on the major axis or diameter. The folded IOL then may be gripped, for example, by the tongs of a small and delicate forceps 26 for removal from the device as shown in FIG. 2.

Figure 3:
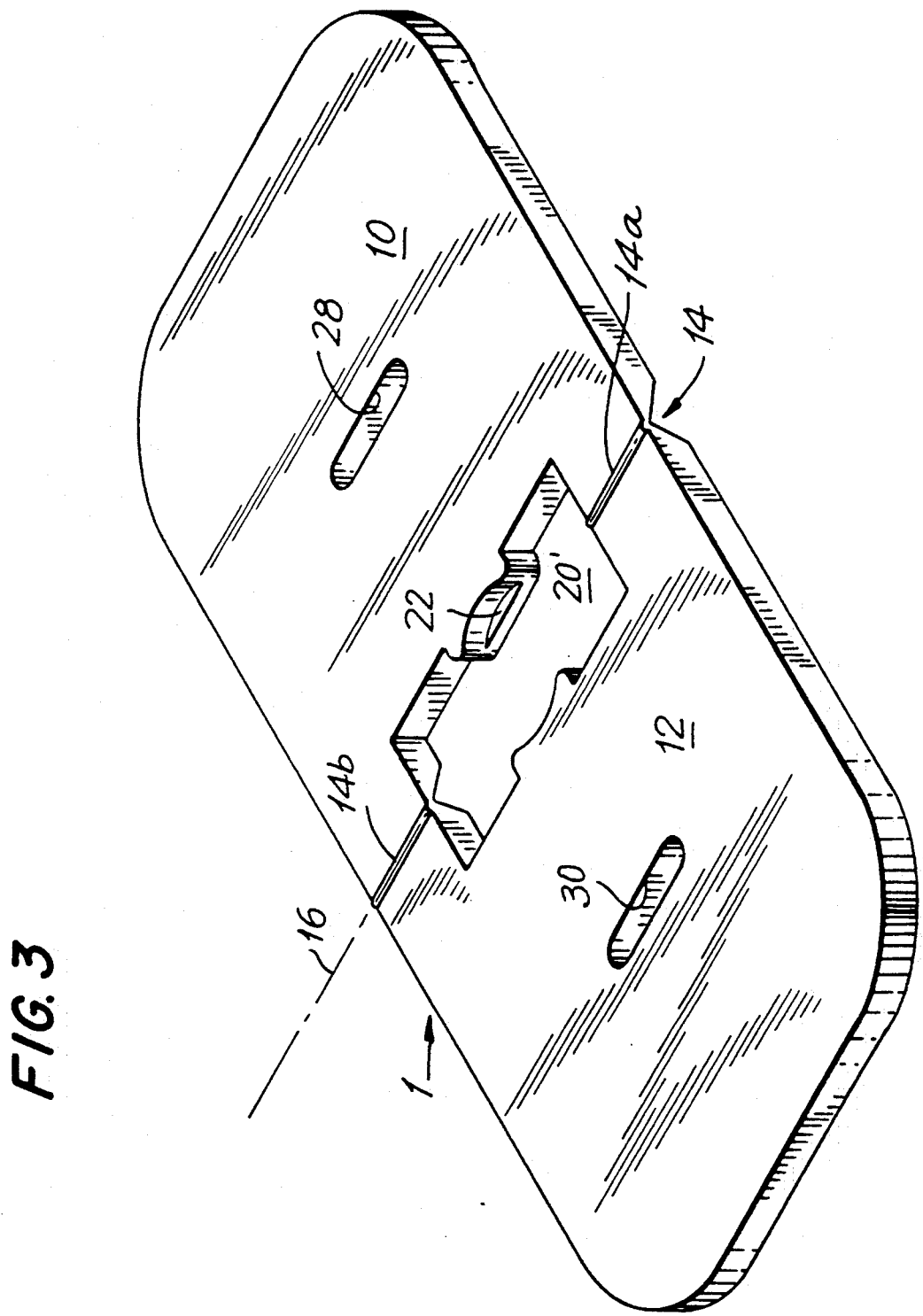
FIG. 3 is an enlarged perspective view of an second embodiment of the present invention in an unfolded condition.
Figure 4:
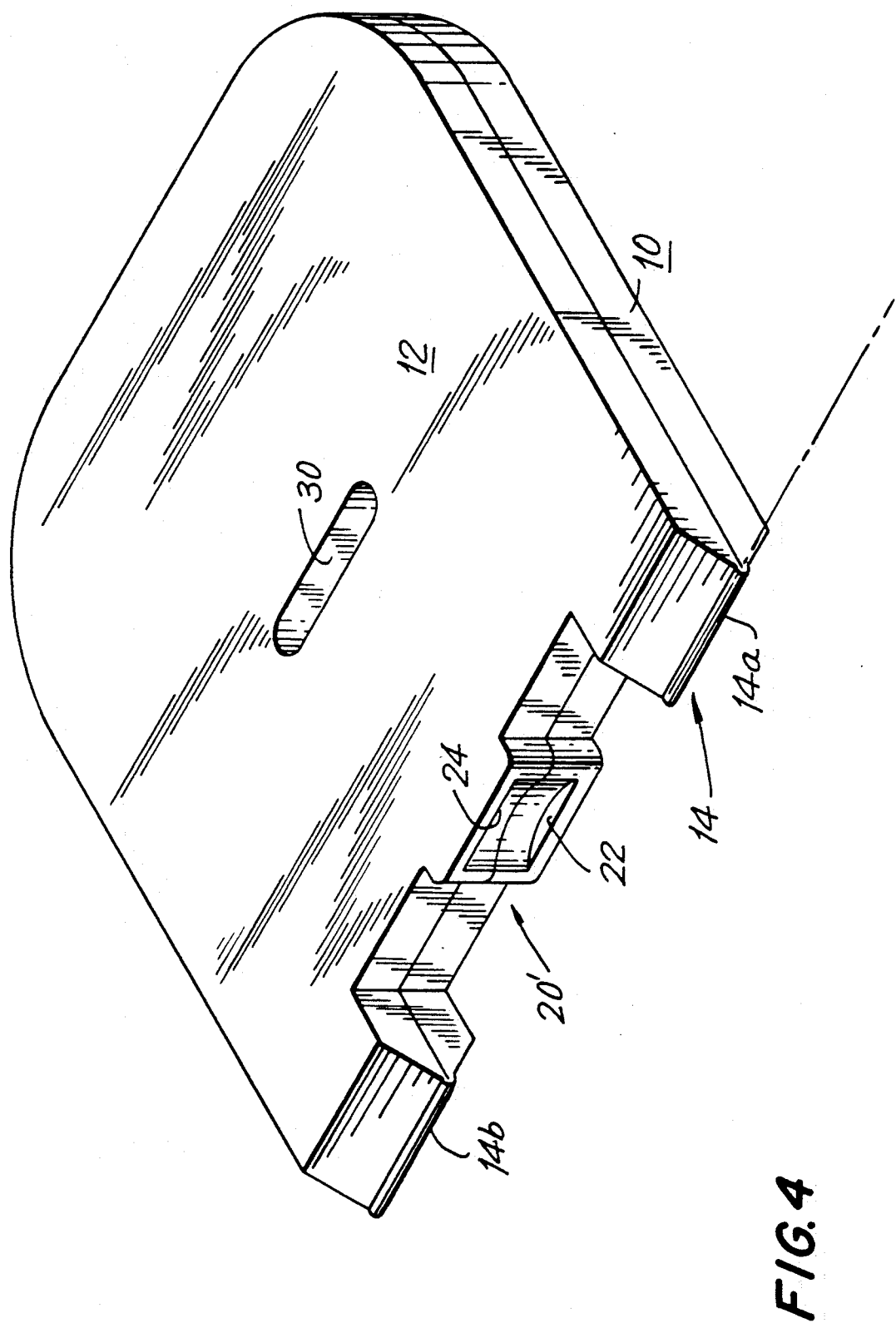
FIG. 4 is an enlarged perspective view of the device of FIG. 3 in a folded condition.
Figure 5:
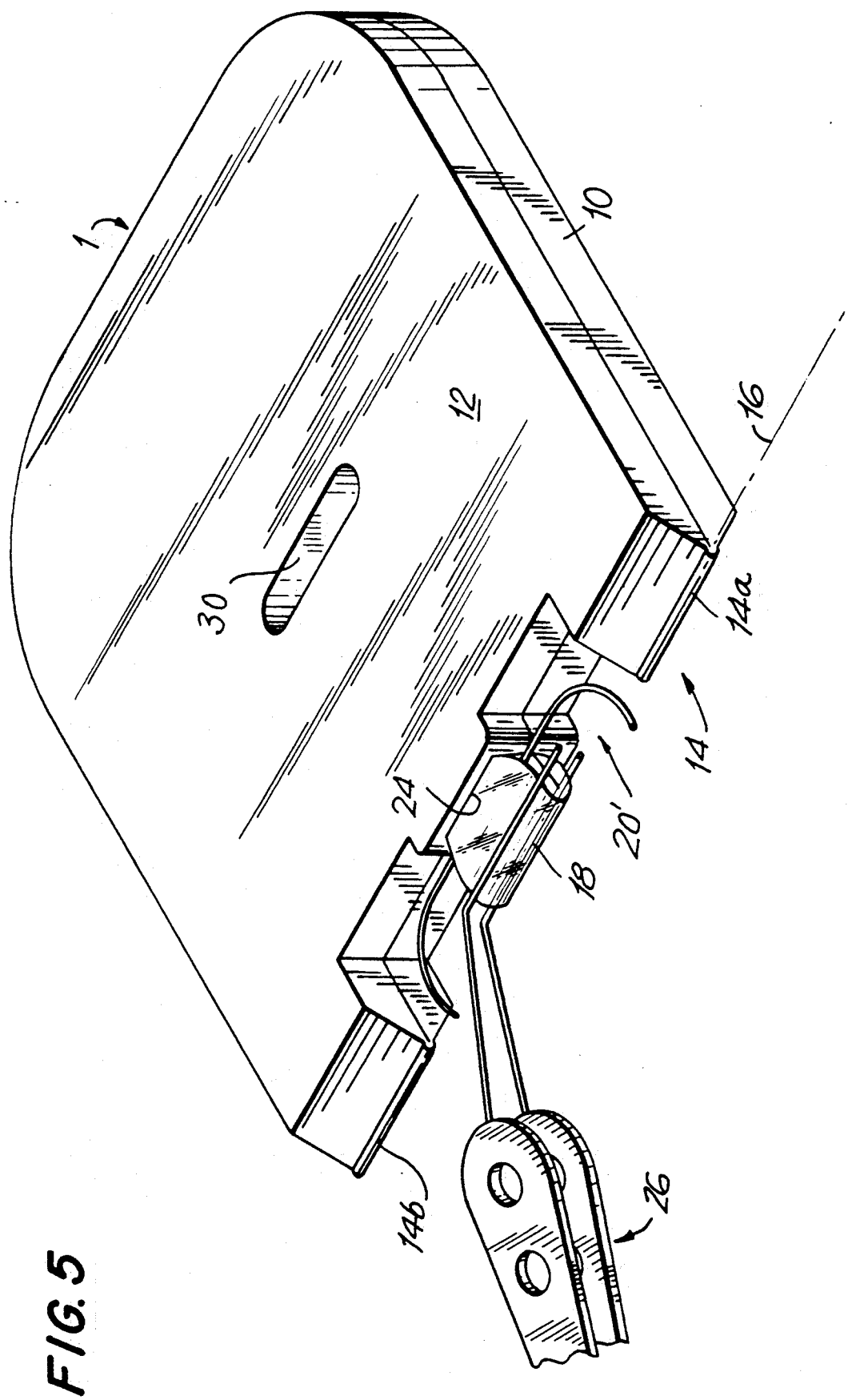
FIG. 5 is an enlarged perspective view of the device of FIG. 4 with an IOL folded along a diameter thereof and forceps gripping the folded IOL for removal from the device.

A second embodiment of the device of the present invention is shown in FIGS. 3, 4 and 5. According to that embodiment of the device, slot 20' rather than being open ended as was slot 20 in FIGS. 1 and 2, extends between opposite end portions 14a and 14b of the hinge means 14. Also, the opposing semicircular shoulders 22 and 24 supporting the IOL optic are formed in ear-shaped portions of the inner edges of the slot 20'. In addition, the sections 10 and 12 include openings 28 and 30 for receiving positioning tabs 32 extending from a case 34 for the device such as the one illustrated in FIG. 6.

Figure 6:
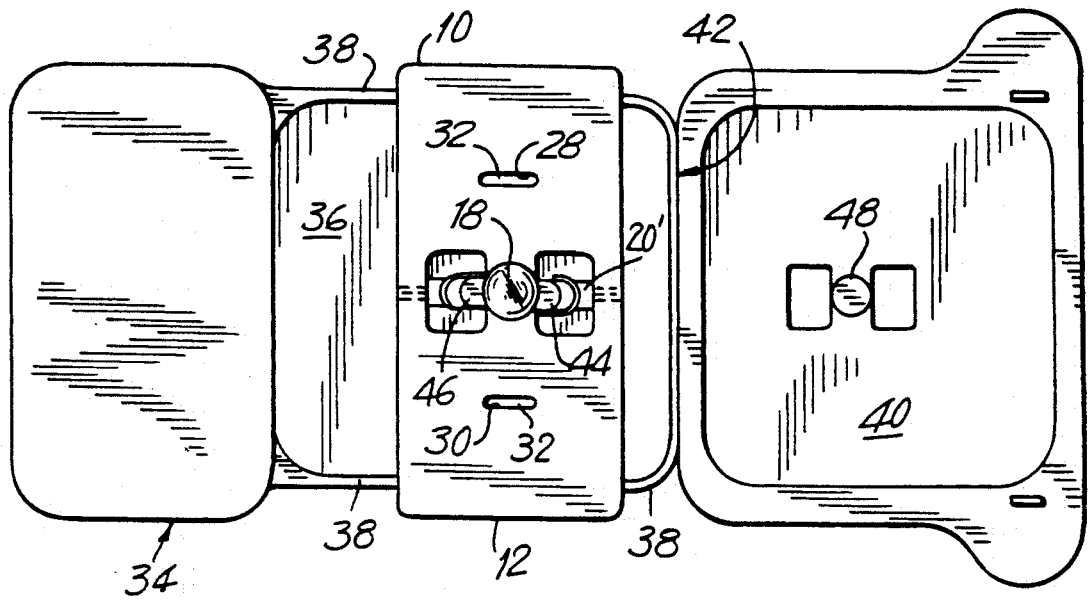
FIG. 6 is a top view of the device of FIG. 3 in an open shipping case.
Figure 7:
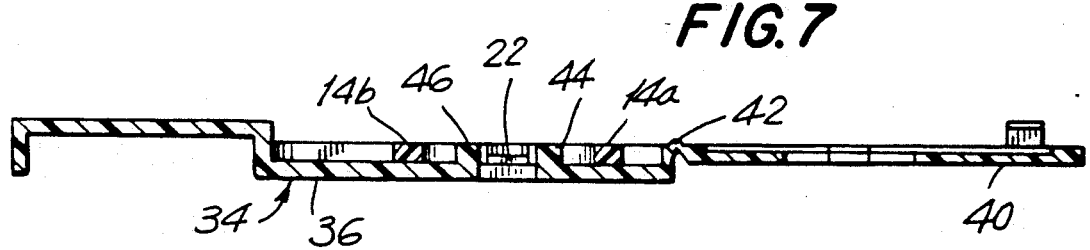
FIG. 7 is section side view of the device and shipping case shown in FIG. 6.
Figure 8:
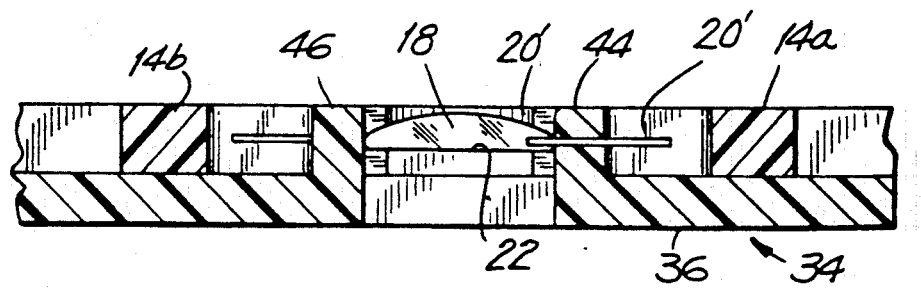
FIG. 8 is an enlarged side sectional view of a portion of the device and shipping case combination shown in FIG. 7 illustrating the manner in which an IOL is supported in its flat or unfolded form within the combination.

In FIG. 6, case 34 is preferably formed of a single piece of material, such as plastic, and includes a flat base 36 having vertically extending side rails 38 for supporting sections 10 and 12 of the device in its unfolded condition. Flat top 40 is hinged at 42 to the base to fold over, cover and secure the IOL 18 held in the device. In this regard, as shown most clearly in FIGS. 6, 7 and 8, vertical stabilizing tabs 44 and 46 extend upward from base 36 through the slot 20' immediately adjacent edges of the IOL optic to combine with shoulders 22 and 24 to provide lateral positioning for the IOL 18. In addition, top 40 carries a ring 48 for positioning over the top of the IOL 18 when the top is folded with the bottom to close the case. This provides vertical stability for the IOL in the device of the present invention when mounted in the case. Other cases can be utilized with the device of present invention for shipping the IOL flat in the device of the present invention or folded in the device of the present invention. The device and case combination provides a stable, secure position for the IOL 18 during shipment as well as in storage awaiting use of the IOL in implant surgery.

Figure 9:
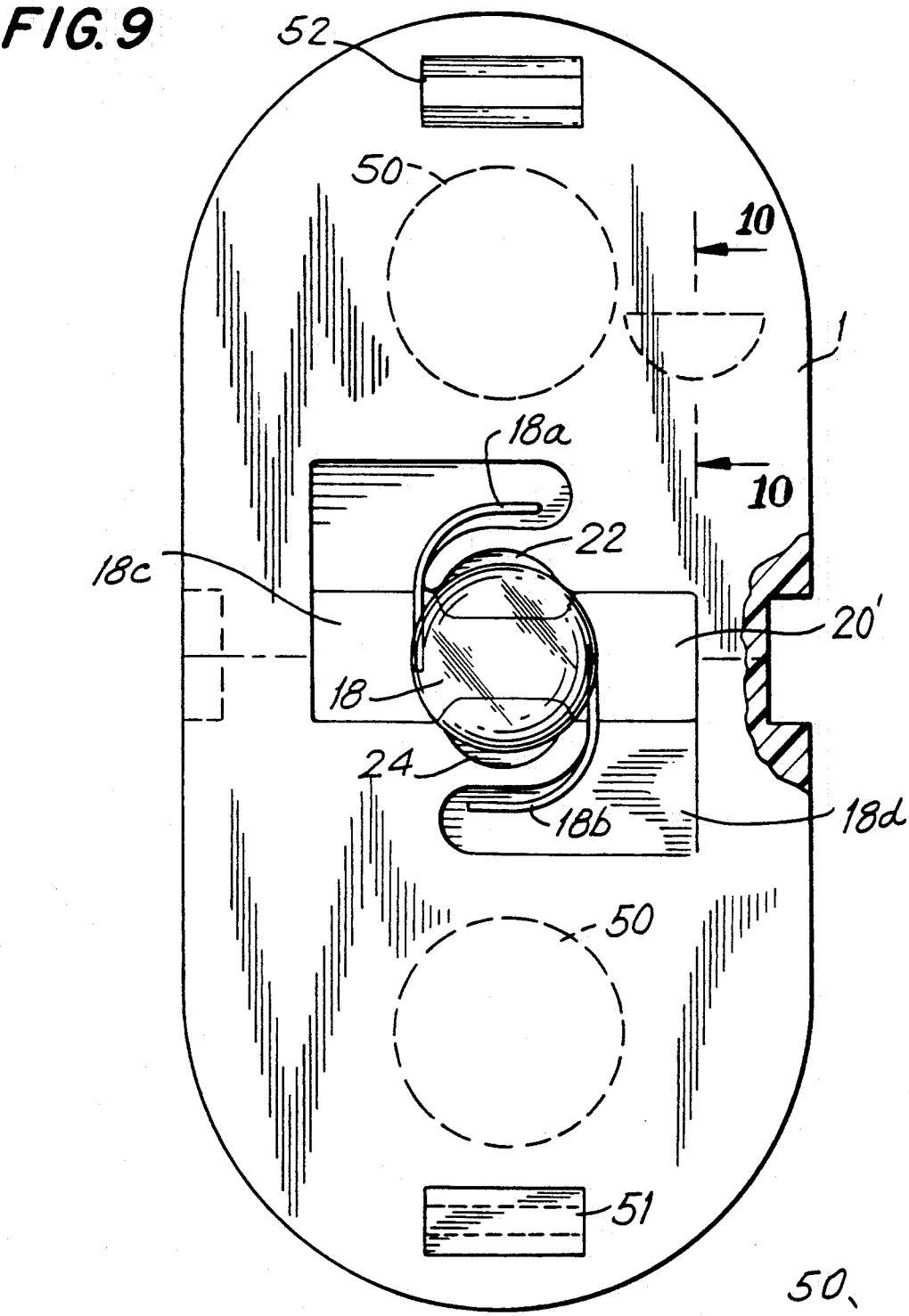
FIG. 9 is an enlarged top view of a further embodiment of the present invention holding an IOL with two loops or haptics and having means for locking the device in the folded position.

FIG. 9 shows a further embodiment of the device of the present invention which is characterized by having a support for haptics 18a and 18b shown at 18c and 18d. In addition, finger depressions 50 are disposed on the underside of the device to assist in folding the IOL within the device. Protusion 51 locks into slot or opening 52 so that the device secures the IOL in a folded position. The remainder of the design of device 1 is similar to that described above.

Figure 10:
FIG. 10 is a section taken along lines 10/10 of FIG. 9.

FIG. 10 is a section along lines 10/10 of FIG. 9.

Figure 11:
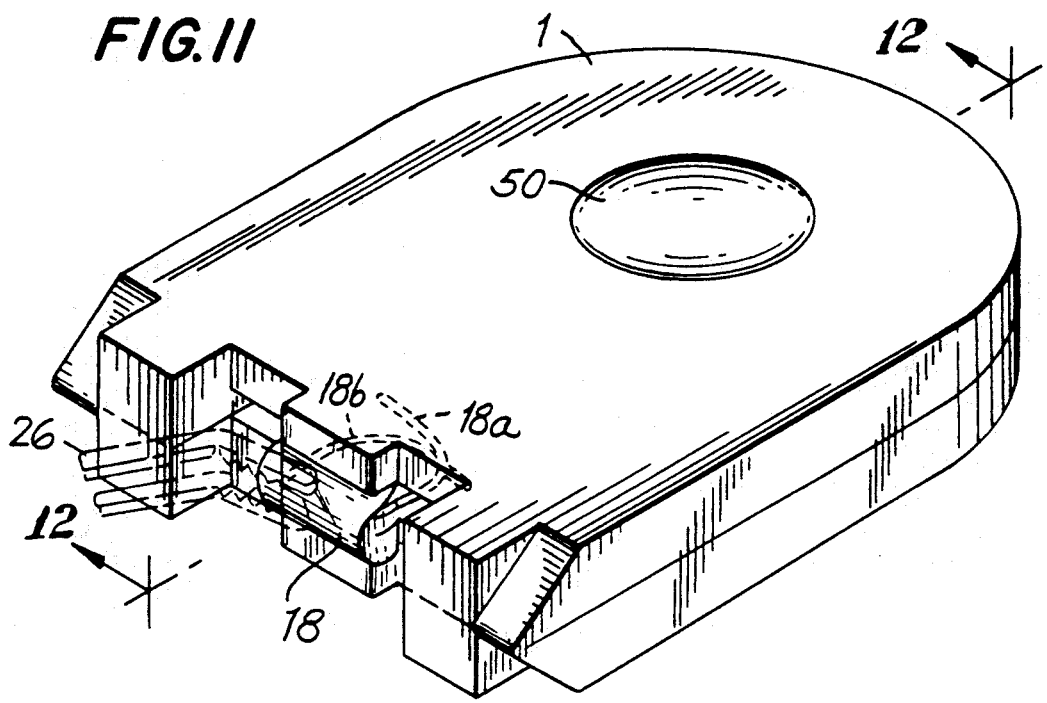
FIG. 11 shows the device of FIG. 9 in a folded state.

FIG. 11 shows the device of FIGS. 9 and 10 having an IOL with two loops or haptics 18a and 18b folded within the device. Forceps 26 or a similar instrument is shown as gripping the edge of the folded IOL for removal.

Figure 12:
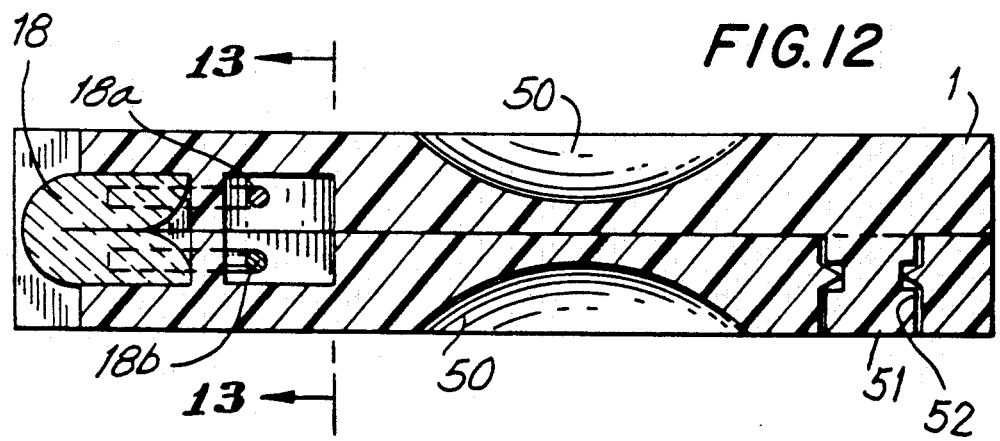
FIG. 12 is a sectional view taken along lines 12/12 of FIG. 11.
Figure 13:
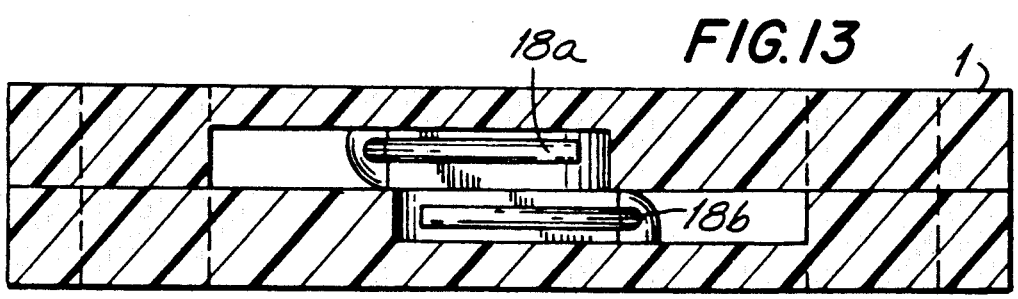
FIG. 13 is a sectional view taken along lines 13/13 of FIG. 12.

FIG. 12 is a section taken along lines 12/12 of FIG. 11. FIG. 13 is a section taken along lines 13/13 of FIG. 12. These figures show the finger depressions 50 and the IOL and haptics in the folded position.

Figure 14:
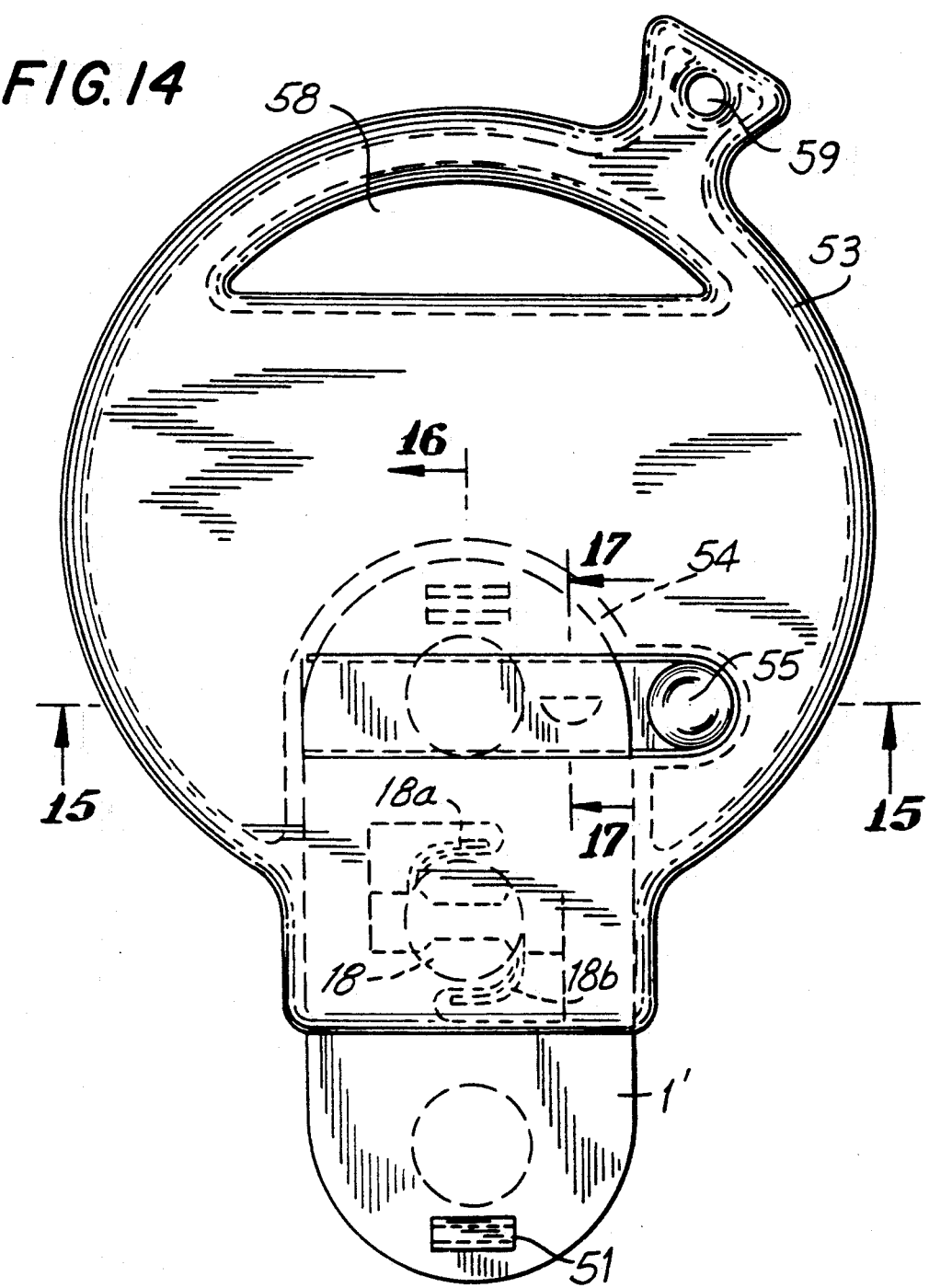
FIG. 14 shows the embodiment of FIGS. 9 to 13 in a case suitable for transporting the device with an IOL in the unfolded state.
Figure 15:
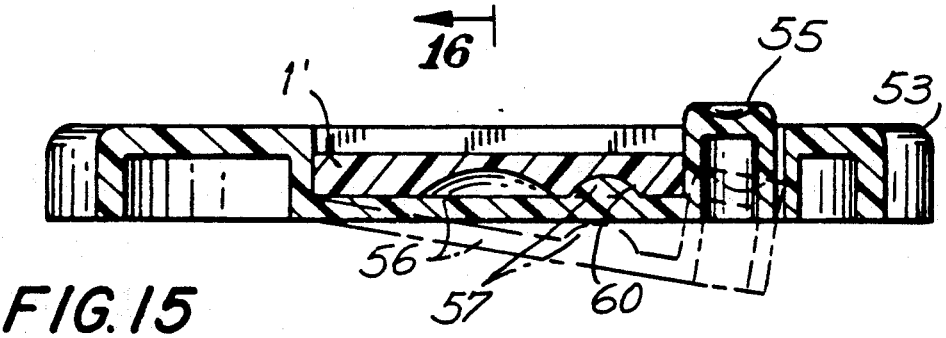
FIG. 15 is a section taken along lines 15/15 of FIG. 14.
Figure 20:
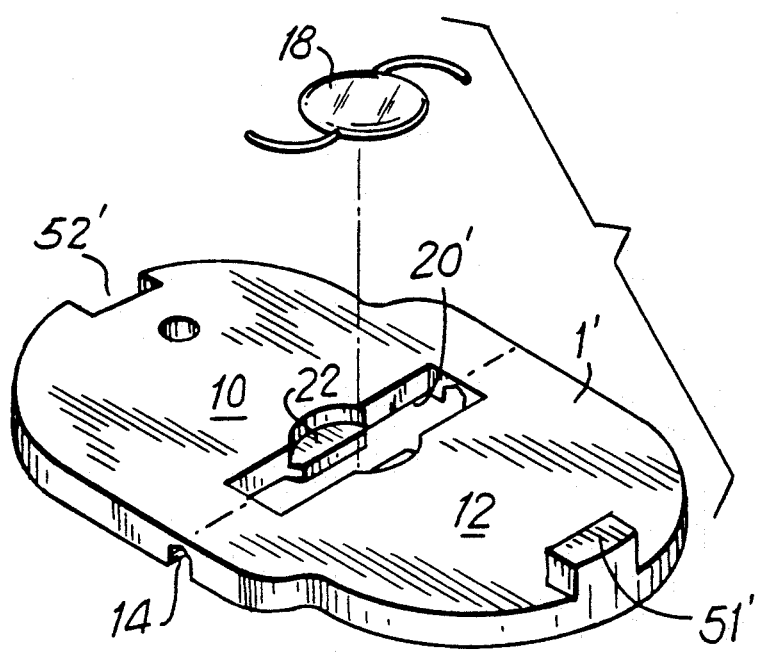
FIG. 20 shows a further embodiment of the device of the present invention.
Figure 21:
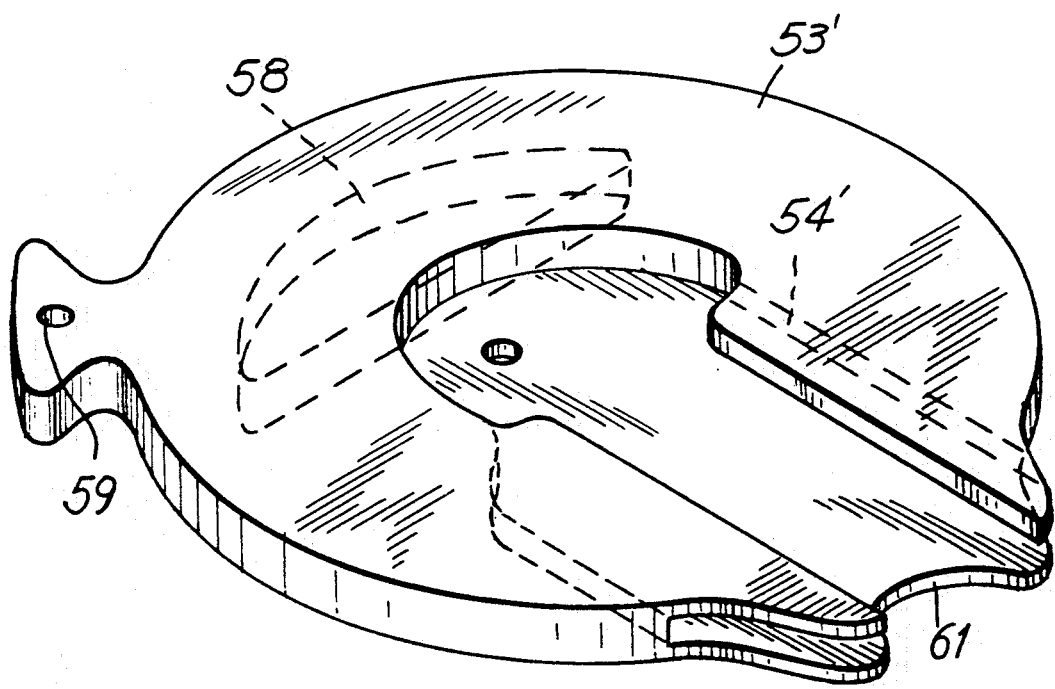
FIG. 21 shows a further embodiment of the case of the present invention for receiving the device of the present invention with an IOL in an unfolded state.

FIGS. 14 to 19 show a further embodiment of the present invention wherein the device is fitted into a carrying or transportation case whereby the device holds an IOL having two loops or haptics 18a and 18b in an unfolded state. According to this embodiment, the device shown in FIG. 9 slides in a slot 54 in case 53. It is locked in place through arm 56, locking member 57, locking member recess 60 and release member 55 which when the device 1' is slid into slot 54 locks the release member into place by movement of member 57 into recess 60. The device 1' is released from case 54 by pressing down on release member 55 which moves locking member 57 out of recess 60 as shown in FIG. 15. Case 53 may have a cut-out portion or recess 58 and an eyelit 59. Cut-out or recess 58 is a convenient place to put a trademark or logo. It can also be used as a convenient trough to wash or clean the lens.

FIGS. 16 and 17 are sections taken along lines 16/16 and 17/17 respectively of FIG. 14.

FIG. 18 shows a further embodiment according to the present invention where device 1' holding an IOL lens body 18 having haptics or loops 18a and 18b is slid into slot 54, but in this embodiment, device 1' is held within slot 54 by a slip or friction fit.

FIG. 19 is a section taken along lines 19/19 of FIG. 18 and shows finger depressions 50, protrusion 51 and slot 52 for device 1' which locks the device into a folded state.

FIG. 20 to 23 show a further embodiment of the present invention where device 1' slides into case 53' by placement in slot 54'. The case 53' has a curved portion 61' which allows the end of device 1' having protuberance 51 to extend slightly beyond the end of the slot and is grippable in order to facilitate removable of device 1' from slot 54'. While these figures show a friction fit arrangement, this arrangement is also adaptable to the release member 55, arm 56 locking member 57 and locking member recess 60 shown in FIGS. 14 and 15.

Other and further uses of the device and the method according to the present invention will be more fully appreciated by those skilled in the art by reference to the foregoing specification, the drawings and the appended claims.

What is claimed is:

1. A device for folding an IOL and thereafter holding it in its folded state, which comprises a member foldable into two sections of substantially equal dimensions, each of said sections having a recessed shoulder portion dimensioned to receive an edge of the optic of an unfolded IOL and to hold the IOL in the plane of the member when the member is in an unfolded state.

2. A device according to claim 1 which further comprises a slot substantially symmetrically disposed along a portion of the fold line of said member.

3. A device according to claim 2 wherein said slot extends beyond said shoulder portions.

4. A device according to claim 3 in combination with a case therefore suitable for transporting said device having an unfolded IOL therein, said case having a slot therein for receiving said device with the IOL therein said slot being configured to enable a portion of said device to be gripped for removal and means for retaining said device within said slot until it is desired to remove it.

5. A device according to claim 2 wherein the slot begins at the outer edge of said member and extends beyond said shoulders.

6. A device according to claim 5 in combination with a case therefore suitable for transporting said device having an unfolded IOL therein, said case having a slot therein for receiving said device with the IOL therein said slot being configured to enable a portion of said device to be gripped for removal and means for retaining said device within said slot until it is desired to remove it.

7. A device according to claim 2 wherein the slot is disposed about the area of each of said shoulder portions, so that the shoulder portions are centrally disposed within said slot.

8. A device according to claim 1 in combination with a case therefore suitable for transporting said device having an unfolded IOL therein, said case having a slot therein for receiving said device with the IOL therein said slot being configured to enable a portion of said device to be gripped for removal and means for retaining said device within said slot until it is desired to remove it.

9. A device according to claim 2 in combination with a case therefore suitable for transporting said device having an unfolded IOL therein, said case having a slot therein for receiving said device with the IOL therein said slot being configured to enable a portion of said device to be gripped for removal and means for retaining said device within said slot until it is desired to remove it.

10. A device according to claim 1 wherein each of said shoulder portions are semicircular.

11. A device according to claim 10 in combination with a case therefore suitable for transporting said device having an unfolded IOL therein, said case having a slot therein for receiving said device with the IOL therein said slot being configured to enable a portion of said device to be gripped for removal and means for retaining said device within said slot until it is desired to remove it.

12. A device according to claim 1 wherein the shoulders are triangular.

13. A device according to claim 12 in combination with a case therefore suitable for transporting said device having an unfolded IOL therein, said case having a slot therein for receiving said device with the IOL therein said slot being configured to enable a portion of said device to be gripped for removal and means for retaining said device within said slot until it is desired to remove it.

14. A device according to claim 1 wherein the shoulders are rectangular.

15. A device according to claim 14 in combination with a case therefore suitable for transporting said device having an unfolded IOL therein, said case having a slot therein for receiving said device with the IOL therein said slot being configured to enable a portion of said device to be gripped for removal and means for retaining said device within said slot until it is desired to remove it.

16. A device according to claim 1 wherein the sections are beveled along the fold line of the member.

17. A device according to claim 16 wherein the beveled portion of each section is on the side which lies on the outside of said device when the device is in a folded position.

18. A device according to claim 11 in combination with a case therefore suitable for transporting said device having an unfolded IOL therein, said case having a slot therein for receiving said device with the IOL therein said slot being configured to enable a portion of said device to be gripped for removal and means for retaining said device within said slot until it is desired to remove it.

19. A device according to claim 16 in combination with a case therefore suitable for transporting said device having an unfolded IOL therein, said case having a slot therein for receiving said device with the IOL therein said slot being configured to enable a portion of said device to be gripped for removal and means for retaining said device within said slot until it is desired to remove it.

20. A device according to claim 1 which further comprises means for locking said device in the folded position.

21. A device according to claim 20 in combination with a case therefore suitable for transporting said device having an unfolded IOL therein, said case having a slot therein for receiving said device with the IOL therein said slot being configured to enable a portion of said device to be gripped for removal and means for retaining said device within said slot until it is desired to remove it.

22. A device according to claim 1 in combination with a case which is suitable for transporting said device having an IOL which is unfolded therein or has a folded IOL therein.

23. A device according to claim 1 in combination with a case therefore suitable for transporting said device having an unfolded IOL therein, said case comprising a base for supporting said member and a top secured to said base in a foldable manner, and means for securing said device in said case, whereby in use said top folds over and covers and secures the folded IOL.

24. The combination according to claim 23 wherein the case further comprises IOL stabilizing means extending from the base through the slot adjacent the IOL.

25. The combination according to claim 24 wherein the device has an opening through each section and the case further comprises means having a configuration on one portion to match the periphery of the optic, said means extending from one of the base or top made with openings in the device to secure the device in the case.

26. The combination according to claim 24 which further comprises a second IOL stabilizing means attached to the top of the case for securing the IOL in the device when the top is folded over the base.

27. A device according to claim 1 in combination with a case therefore suitable for transporting said device having an unfolded IOL therein, said case having a slot therein for receiving said device with the IOL therein said slot being configured to enable a portion of said device to be gripped for removal and means for retaining said device within said slot until it is desired to remove it.

28. A combination according to claim 27 wherein said means comprises a friction fit between said device and said slot.

29. A combination according to claim 27 wherein said case has a locking member recess and a release member slot, and said means comprises an arm movably secured to the underside of said case, a locking member on said arm sized to fit in the locking member recess and a release member sized to fit movably in said release member slot.

30. A method of folding a foldable IOL along a diameter thereof which comprises placing said IOL in the device of claim 1 so that the edges of the optic rest on the shoulders and the optic is substantially centered along the fold line of said member, and folding said sections together.

* * * * *